(12) United States Patent
Breashears

(10) Patent No.: US 7,563,238 B1
(45) Date of Patent: Jul. 21, 2009

(54) ORTHOPEDIC BOOT

(76) Inventor: Jack W. Breashears, 2721 Mt. Moriah Rd., Pell City, AL (US) 35125

( * ) Notice: Subject to any disclaimer, the term of this patent is extended or adjusted under 35 U.S.C. 154(b) by 337 days.

(21) Appl. No.: 11/502,722

(22) Filed: Aug. 14, 2006

(51) Int. Cl.
*A61F 5/00* (2006.01)

(52) U.S. Cl. .............................. 602/27; 602/5; 602/16; 602/23

(58) Field of Classification Search ............. 602/5, 602/16, 27–29, 23, 60–65; 36/140; 128/882; D24/192

See application file for complete search history.

(56) References Cited

U.S. PATENT DOCUMENTS

| 5,370,203 | A | * | 12/1994 | Kiska | 182/111 |
| 5,429,588 | A | * | 7/1995 | Young et al. | 602/27 |
| 5,954,074 | A | * | 9/1999 | Mattson | 135/68 |
| 6,155,998 | A | * | 12/2000 | Gilmour | 602/27 |
| 6,648,843 | B1 | * | 11/2003 | Marciano et al. | 602/27 |

* cited by examiner

*Primary Examiner*—Kim M Lewis

(57) ABSTRACT

An illustrative embodiment of the orthopedic boot includes a boot frame having a sole portion and a pair of spaced-apart adjusting frame elements carried by the sole portion. A boot is carried by the boot frame.

4 Claims, 6 Drawing Sheets

ORTHOPEDIC BOOT

FIELD

The present invention relates to orthopedic devices. More particularly, the present invention relates to an orthopedic boot which facilitates enhanced foot support for persons having lower extremity disabilities or injuries.

BACKGROUND

The feet and ankles are vulnerable to a variety of short-term and long-term disabilities or injuries. For example, sprained ankles are common among physically active persons. Such disabilities render it difficult for afflicted persons to walk due to the lack of support to the foot and/or ankle. Therefore, an orthopedic boot is needed which is comfortable and provides ample support to the foot and/or ankle of a person afflicted with a lower extremity injury or disability.

SUMMARY

The present invention is generally directed to an orthopedic boot. An illustrative embodiment of the orthopedic boot includes a boot frame having a sole portion and a pair of spaced-apart adjusting frame elements carried by the sole portion. A boot is carried by the boot frame.

BRIEF DESCRIPTION OF THE DRAWINGS

The invention will now be described, by way of example, with reference to the accompanying drawings, in which.

DETAILED DESCRIPTION

Figure 1:
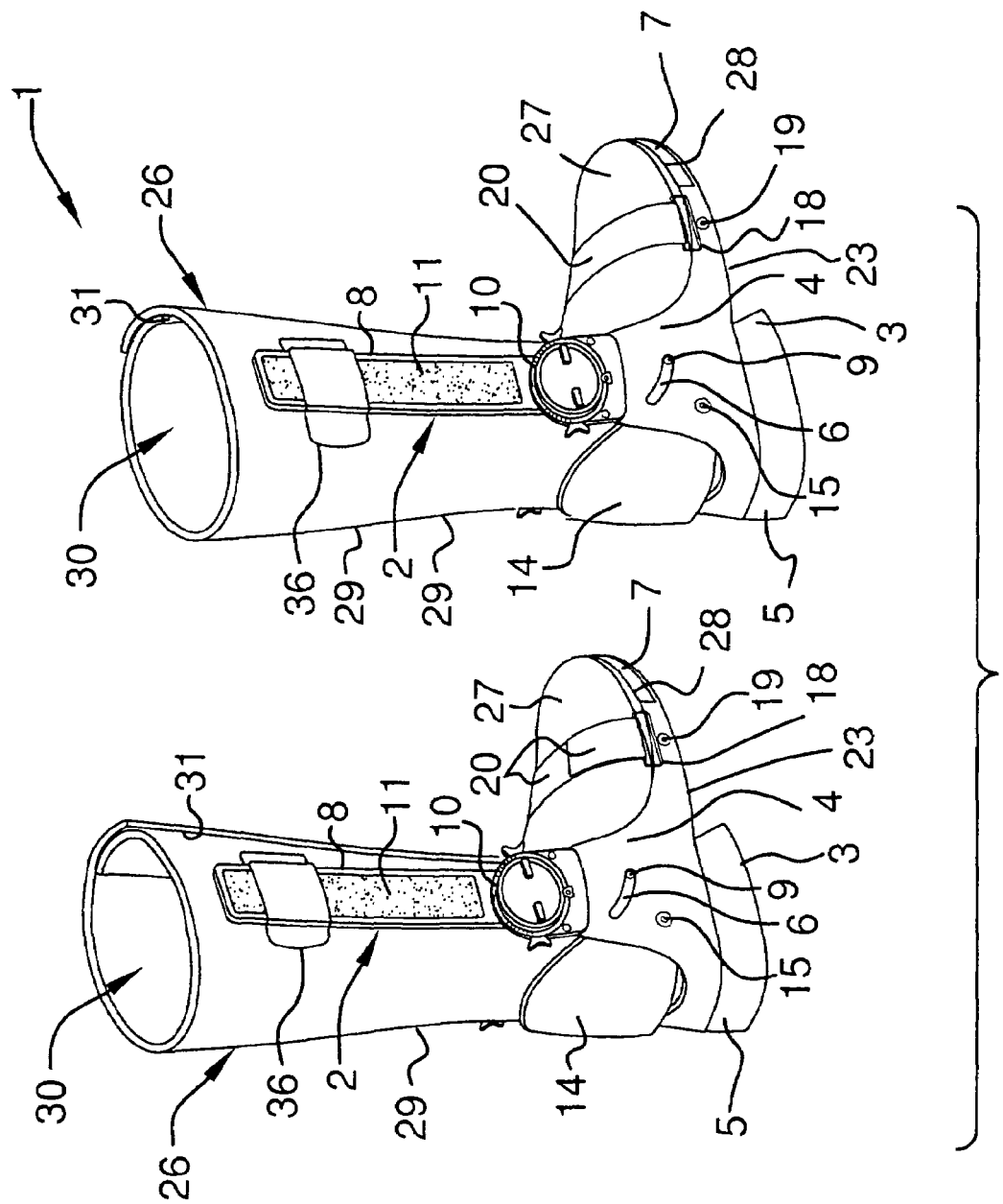
FIG. 1 is a perspective view of an illustrative embodiment of a pair of orthopedic boots.

Referring to the drawings, an illustrative embodiment of the orthopedic boot is generally indicated by reference numeral 1, a pair of which is shown in FIG. 1. The orthopedic boot 1 includes a boot frame 2 and a flexible boot 26 which has a foot portion 27 and an ankle portion 29 and is supported by the boot frame 2, as shown in FIG. 1 and will be hereinafter described. In some embodiments, the boot frame 2 can be adjusted to support the ankle portion 29 at a selected angle with respect to the foot portion 27 of the boot 26, typically in a manner which will be hereinafter described. The boot 26 provides a padded, wraparound support function for the ankle and foot (not shown) of a user to facilitate proper forward walking progression in persons afflicted with lower extremity disabilities or injuries.

Figure 5:
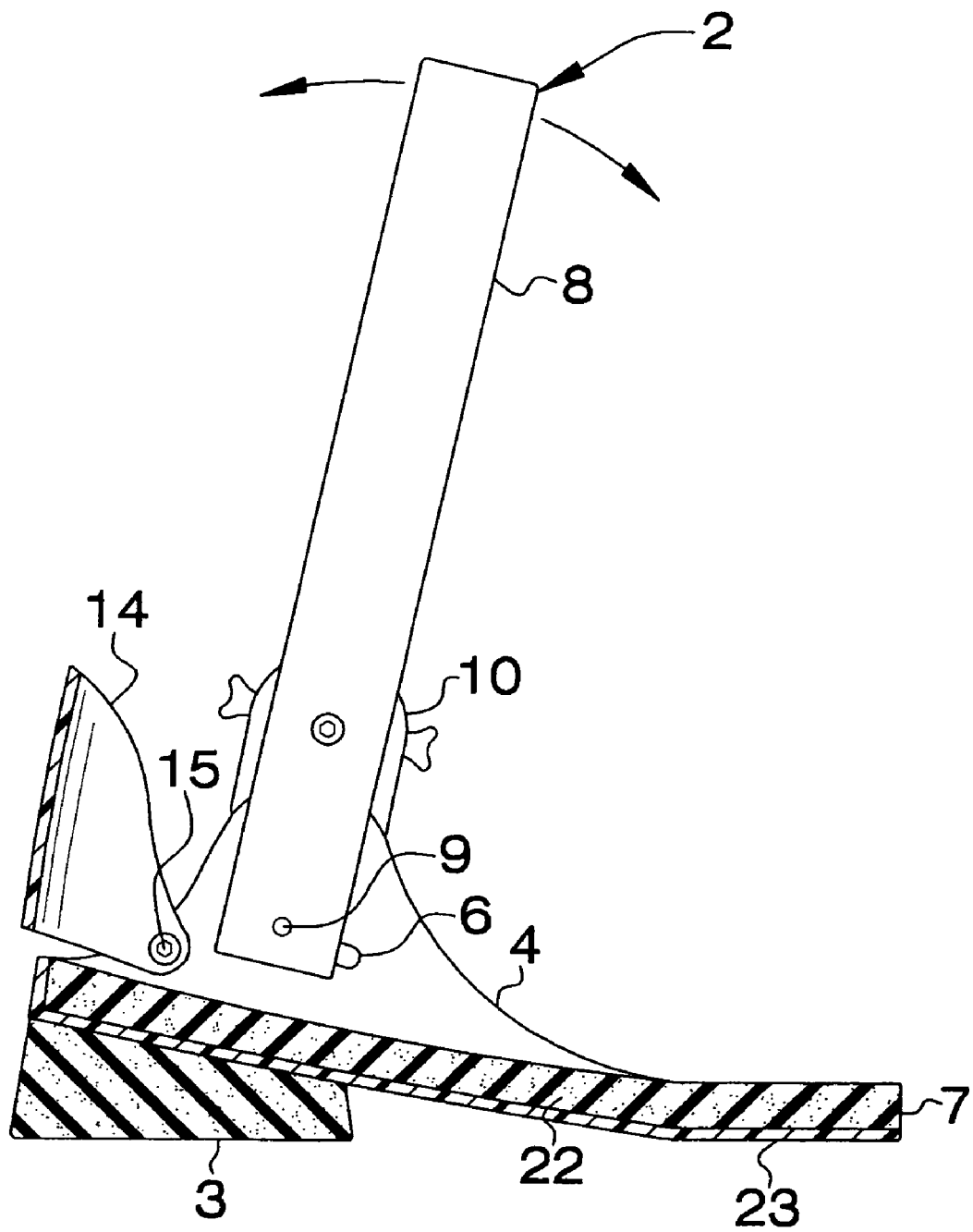
FIG. 5 is a sectional view, taken along section lines 5-5 in FIG. 4, of a boot frame element of an illustrative embodiment of the orthopedic boot.

The boot frame 2 of the orthopedic boot 1 typically includes an elongated sole portion 22, as shown in FIG. 5. The sole portion 22 is typically a resilient rubber or plastic material. The sole portion 22 may be supported by a sole plate 23 which is typically metal or plastic. A toe portion 7 extends from the forward end of the sole portion 22. Foot fastening straps 20, the purpose of which will be hereinafter described, are typically provided on the toe portion 7. A pair of buckles 18 is typically attached to opposite sides of the toe portion 7, typically via buckle fasteners 19. The foot fastening straps 20 are attached to the respective buckles 18 and detachably engage each other typically via hook and loop fasteners (not shown) provided on the respective foot fastening straps 20. A heel 3 may be provided on the bottom surface of the sole plate 23.

Figure 2:
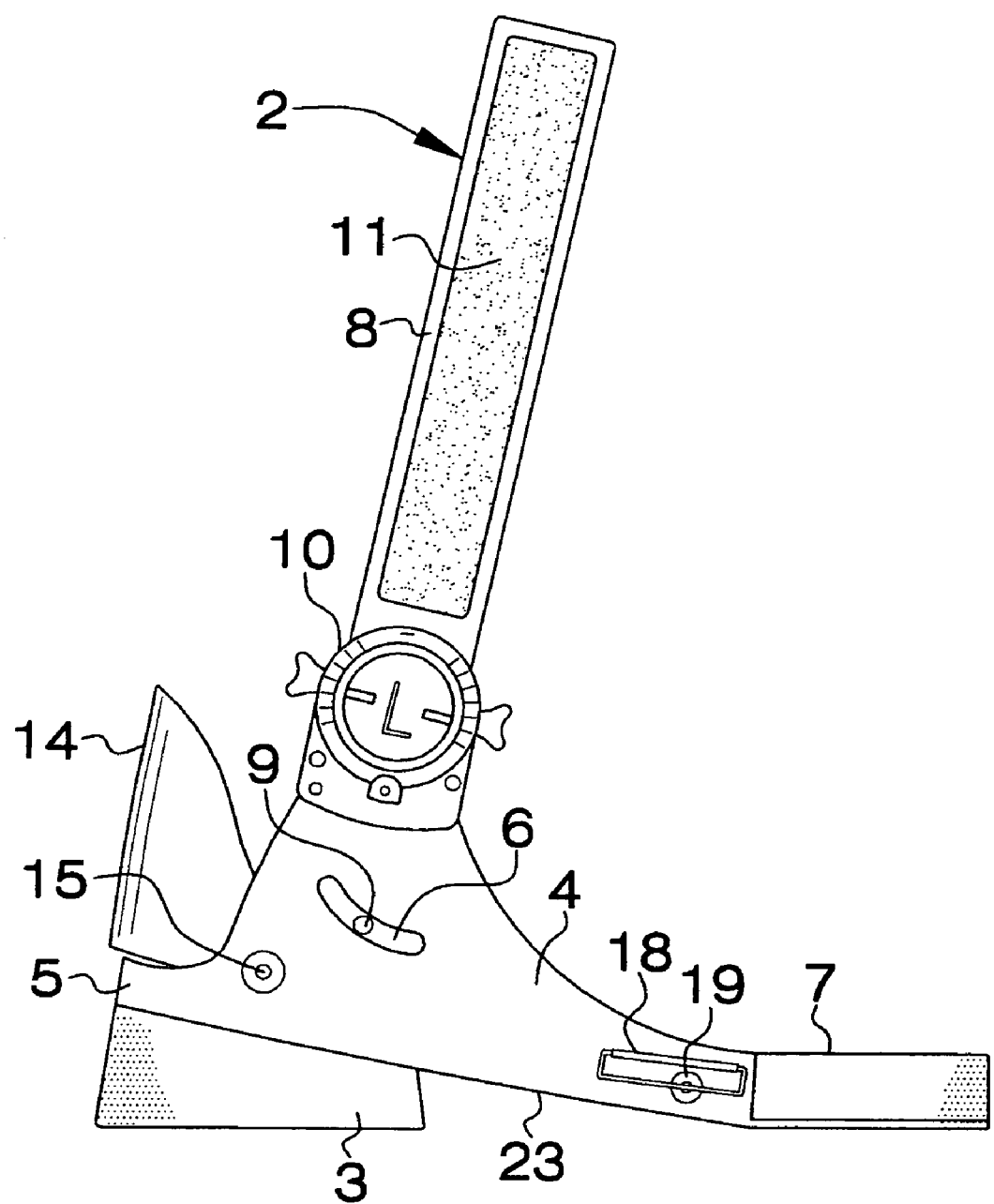
FIG. 2 is a side view of a boot frame element of an illustrative embodiment of the orthopedic boot.
Figure 3:
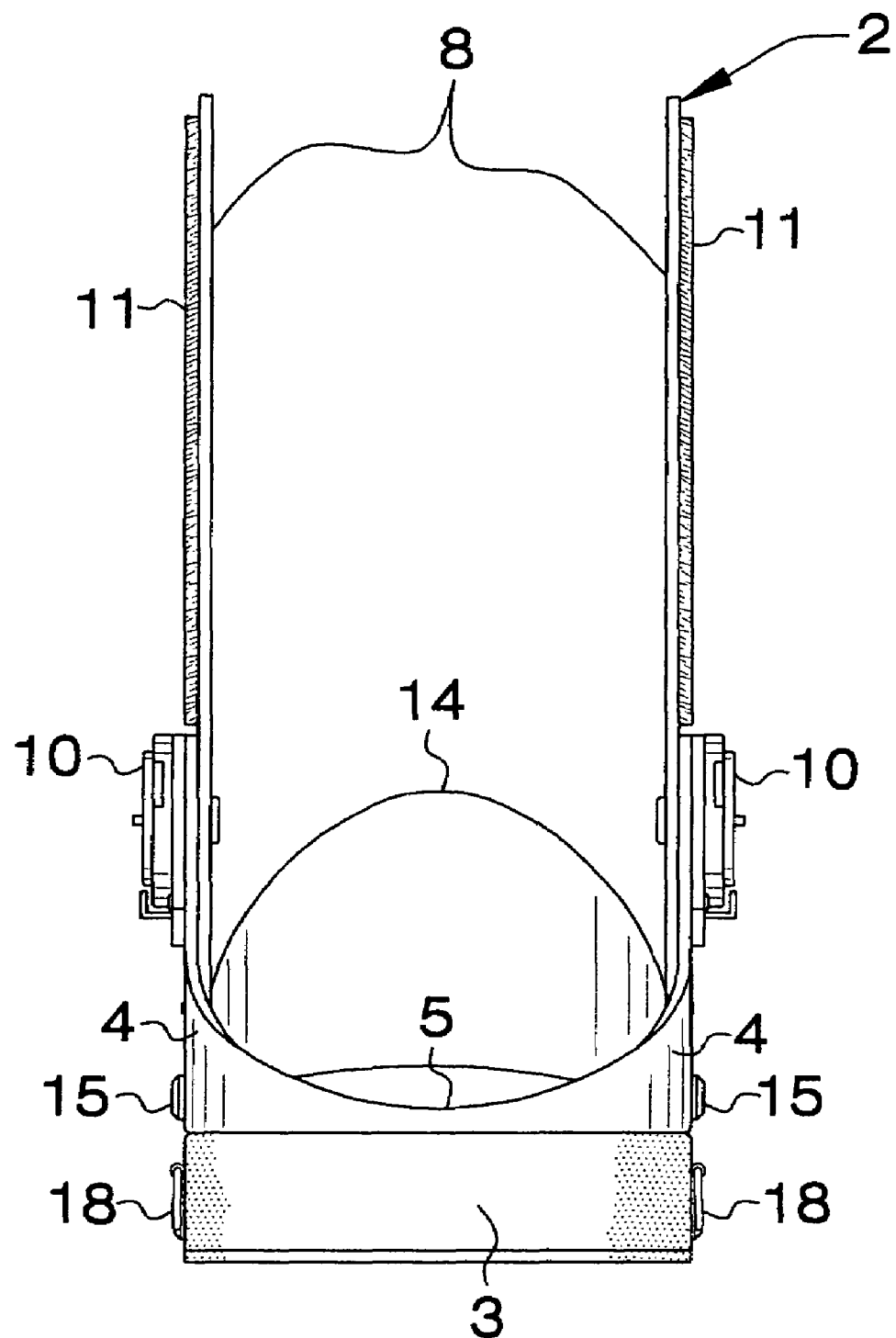
FIG. 3 is a rear view of a boot frame element of an illustrative embodiment of the orthopedic boot.

A pair of spaced-apart side frame portions 4 extends from the sole portion 22. The side frame portions 4 are connected by a connecting frame portion 5, as shown in FIG. 3. A curved pin slot 6 (FIG. 2) is typically provided in each side frame portion 4 for purposes which will be hereinafter described. A curved heel brace 14 extends between the side frame portions 4, above the connecting frame portion 5. The heel brace 14 may be attached to the side frame portions 4 at respective fasteners 15.

Figure 4:
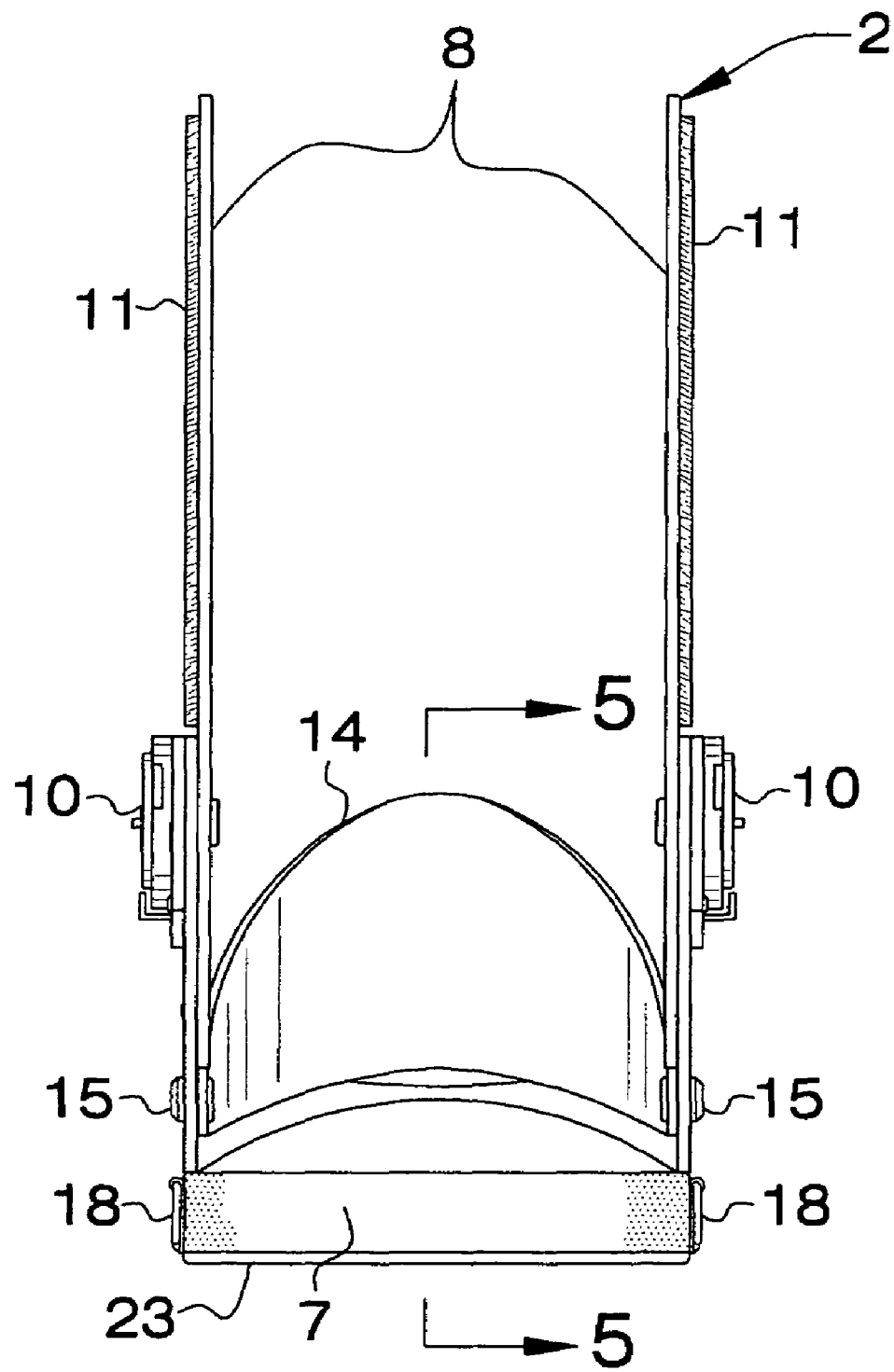
FIG. 4 is a front view of a boot frame element of an illustrative embodiment of the orthopedic boot.

An elongated adjusting frame element 8 extends from each side frame portion 4. The adjusting frame elements 8 extend in generally parallel, spaced-apart relationship with respect to each other, as shown in FIGS. 3 and 4. In some embodiments, each adjusting frame element 8 is angularly adjustable with respect to the corresponding side frame portion 4 from which the adjusting frame element 8 extends. Accordingly, an adjusting frame pin 9 typically extends from each adjusting frame element 8 and is inserted in the pin slot 6 of the corresponding side frame portion 4. An angular adjustment dial 10 is typically provided on each adjusting frame element 8 to facilitate manual adjustment of the angle of each adjusting frame element 8 with respect to the longitudinal axis of the sole portion 22 of the boot frame 2 as the adjusting frame pins 9 traverse the respective pin slots 6. A boot fastener, such as a hook and loop fastener 11, for example, is provided on each adjusting frame element 8 for purposes which will be hereinafter described.

Figure 6:
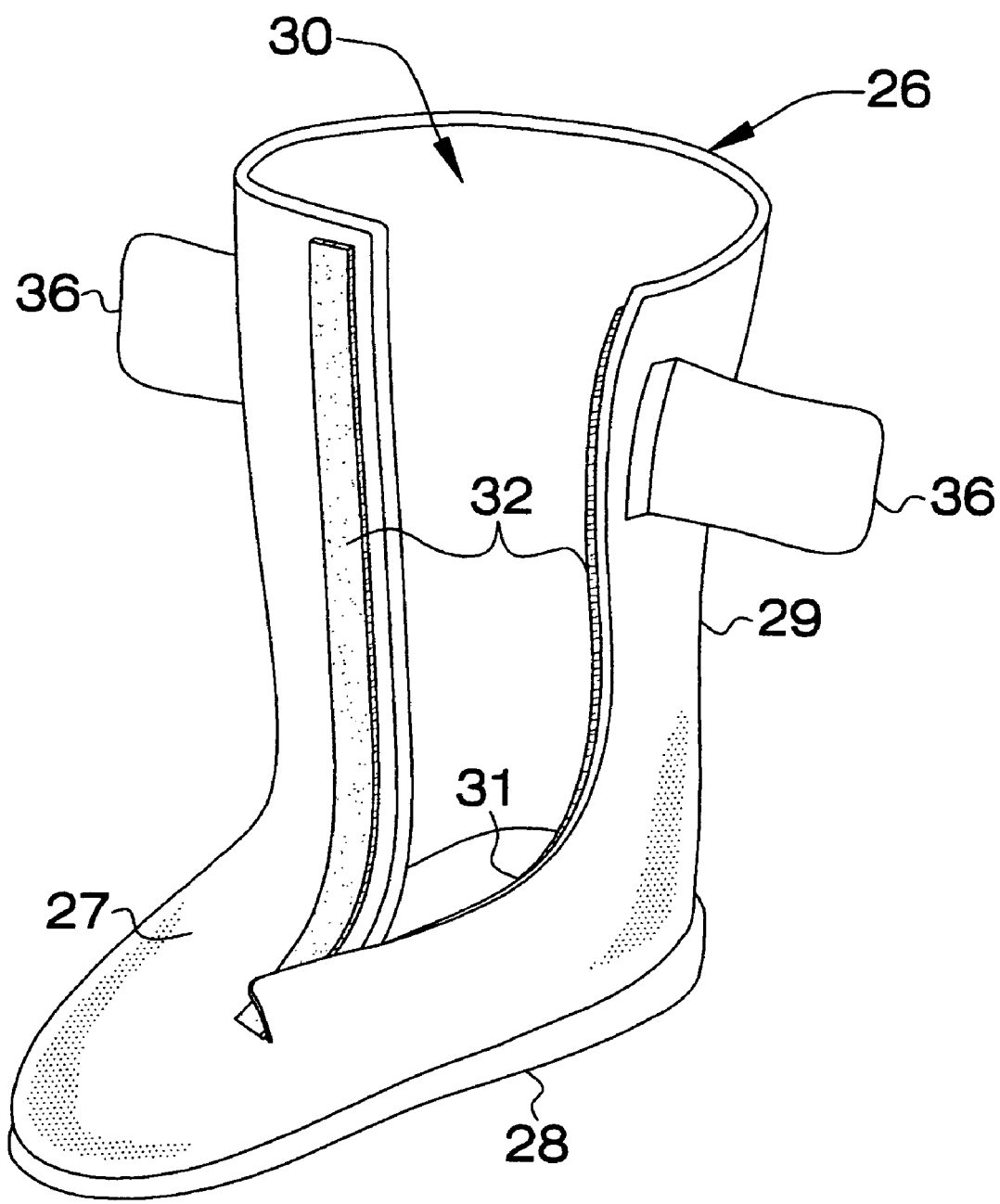
FIG. 6 is a front perspective view of a boot element of an illustrative embodiment of the orthopedic boot.

As shown in FIG. 6, the boot 26 is a flexible or resilient material and includes a foot portion 27 which may have a sole 28 of flexible rubber, for example. An ankle portion 29 extends from the foot portion 27. The foot portion 27 and the ankle portion 29 enclose a boot interior 30. A boot slit 31 extends through the ankle portion 29 and a portion of the foot portion 27. Fasteners, such as hook and loop fasteners 32, for example, are provided on respective sides of the boot slit 31 to facilitate selective closing of the boot 26 around the foot (not shown) of a wearer of the orthopedic boot 1. Ankle fastening strips 36, the purpose of which will be hereinafter described, extend typically from the ankle portion 29 of the boot 26. Strap fasteners (not shown), such as hook and loop fasteners, for example, are provided on the ankle fastening strips 36 to facilitate detachable attachment of the ankle fastening strips 36 to the respective complementary hook and loop fasteners 11 provided on the adjusting frame elements 8 of the boot frame 2, as will be hereinafter further described.

In typical application, the orthopedic boot 1 is worn by a person (not shown) who is afflicted with lower extremity disabilities or injuries. Accordingly, the boot 26 is inserted in the boot frame 2, with the foot portion 27 of the boot 26 resting on the sole portion 22 of the boot frame 2 and the ankle portion 29 of the boot 26 extending between the side frame portions 4 and adjusting frame elements 8 of the boot frame 2. The ankle fastening straps 36 on the ankle portion 29 of the boot 26 are detachably attached to the hook and loop fasteners 11 provided on the respective adjusting frame elements 8 of the boot frame 2. The foot fastening straps 20 provided on the toe portion 7 of the boot frame 2 are extended over the foot portion 27 of the boot 26 and fastened to each other. In some embodiments, the angular position of the foot portion 27 with respect to the ankle portion 29 of the boot 26 can be selectively adjusted to the desired inclination angle, depending on the comfort needs of the user, by rotating the angular adjustment dial 10 on the boot frame 2. The foot (not shown) of the user is then inserted into the boot interior 30 of the boot 26 until the user's foot extends into the foot portion 27 and the user's ankle extends from the boot 26 through the ankle portion 29. The boot 26 is then closed by attaching the hook and loop fasteners 32 (FIG. 6) on respective sides of the boot slit 31 to each other to fasten the boot 26 to the user's foot and leg. Accordingly, the orthopedic boot 1 facilitates a proper forward walking progression as the boot 26, reinforced by the boot frame 2, provides a padded, wraparound support function to the user's foot and ankle. The heel brace 14 engages the rear area of the foot portion 27 of the boot 26, maintaining the user's foot in the proper position inside the boot 26. The user's foot is removed from the orthopedic boot 1 typically by unfastening the hook and loop fasteners 32 (FIG. 6) and opening the boot slit 31 of the boot 26.

While the preferred embodiments of the invention have been described above, it will be recognized and understood that various modifications can be made in the invention and the appended claims are intended to cover all such modifications which may fall within the spirit and scope of the invention.

What is claimed is:

1. An orthopedic boot, comprising:
    a boot frame having a sole portion, a toe portion extending from said sole portion, a pair of spaced-apart side frame portions extending from said sole portion, a pair of spaced-apart adjusting frame elements pivotally carried by said pair of spaced-apart side frame portions, respectively, and a pair of angular adjustment dials carried by said pair of spaced-apart adjusting frame elements, respectively;
    an adjusting frame pin extending from one of said pair of spaced-apart adjusting frame elements and is inserted in a pin slot of a corresponding one of said pair of spaced-apart frame portions; and
    a boot having a foot portion carried by said sole portion of said boot frame and an ankle portion carried by said foot portion.

2. The orthopedic boot of claim 1 further comprising a heel carried by said sole portion of said boot frame.

3. The orthopedic boot of claim 1 further comprising a heel brace carried by said sole portion of said boot frame.

4. The orthopedic boot of claim 1 further comprising a foot fastening strap carried by said sole portion of said boot frame and extending over said foot portion of said boot and a pair of ankle fastening straps carried by said ankle portion of said boot and engaging said pair of spaced-apart adjusting frame elements, respectively, of said boot frame.

* * * * *